(12) United States Patent
Adkinson et al.

(10) Patent No.: US 8,946,319 B2
(45) Date of Patent: Feb. 3, 2015

(54) BUTYL IONOMERS FOR USE IN REDUCING A POPULATION OF AND/OR PREVENTING ACCUMULATION OF ORGANISMS AND COATINGS MADE THEREFROM

(75) Inventors: Dana Adkinson, London (CA); Lorenzo P. Ferrari, London (CA); J. Scott Parent, Kingston (CA); Ralph A. Whitney, Kingston (CA); Rui Resendes, Kingston (CA)

(73) Assignee: LANXESS International S.A., Granges-Paccot (CH)

( * ) Notice: Subject to any disclaimer, the term of this patent is extended or adjusted under 35 U.S.C. 154(b) by 353 days.

(21) Appl. No.: 13/201,506

(22) PCT Filed: Feb. 5, 2010

(86) PCT No.: PCT/CA2010/000159
§ 371 (c)(1),
(2), (4) Date: Mar. 29, 2012

(87) PCT Pub. No.: WO2010/091499
PCT Pub. Date: Aug. 19, 2010

(65) Prior Publication Data
US 2012/0178848 A1    Jul. 12, 2012

Related U.S. Application Data

(60) Provisional application No. 61/152,436, filed on Feb. 13, 2009, provisional application No. 61/152,432, filed on Feb. 13, 2009.

(51) Int. Cl.
*C09D 5/16* (2006.01)
*C08L 23/28* (2006.01)
*A61L 2/16* (2006.01)
*C08L 23/08* (2006.01)
*C08L 23/36* (2006.01)
*C08L 23/04* (2006.01)
*C08L 23/10* (2006.01)
*C08L 23/16* (2006.01)
*C08L 77/00* (2006.01)

(52) U.S. Cl.
CPC ......... *C08L 23/283* (2013.01); *A61L 2/16* (2013.01); *C08L 23/0876* (2013.01); *C08L 23/36* (2013.01); *C09D 5/1637* (2013.01); *C08L 23/04* (2013.01); *C08L 23/10* (2013.01); *C08L 23/16* (2013.01); *C08L 77/00* (2013.01)
USPC .......................................... 523/122; 523/177

(58) Field of Classification Search
USPC ................................ 523/122, 177; 524/445
See application file for complete search history.

(56) References Cited

U.S. PATENT DOCUMENTS

| | | | |
|---|---|---|---|
| 2,356,128 | A | 8/1944 | Thomas et al. |
| 4,256,857 | A | 3/1981 | Buckler et al. |
| 5,162,445 | A | 11/1992 | Powers et al. |
| 6,060,563 | A | 5/2000 | Peiffer et al. |
| 6,960,632 | B2 | 11/2005 | Kaszas |
| 7,544,722 | B2 | 6/2009 | Boudjouk et al. |
| 2001/0021672 | A1 | 9/2001 | Tsujita |
| 2005/0043440 | A1* | 2/2005 | Resendes et al. ............. 523/201 |
| 2005/0256268 | A1 | 11/2005 | Chen |
| 2006/0062850 | A1 | 3/2006 | Chen et al. |
| 2006/0083710 | A1 | 4/2006 | Joerger et al. |
| 2007/0021529 | A1 | 1/2007 | Boudjouk et al. |
| 2007/0218296 | A1 | 9/2007 | Resendes et al. |
| 2008/0207815 | A1* | 8/2008 | Resendes et al. ............. 524/445 |

FOREIGN PATENT DOCUMENTS

| | | |
|---|---|---|
| CA | 2418884 A1 | 8/2004 |
| CA | 2458741 A1 | 8/2005 |
| CN | 101210061 A | 7/2008 |
| EP | 1835004 A1 | 9/2007 |

OTHER PUBLICATIONS

Supplementary European Search Report from co-pending Application EP10740864 dated May 21, 2012, 2 pages.
International Search Report from co-pending Application PCT/CA2010/000159 dated Feb. 13, 2009, 3 pages.
Morton, Maurice; "Rubber Technology" 3rd Ed., pp. 297-300.
Parent, J. Scott et al; Ion-Dipole Interaction Effects in Isobutylene-Based Ammonium Bromide Ionomers; Journal of Polymer Science, Part A, Polymer Chemistry, vol. 43, pp. 5671-5679.
Parent, J. Scott et al.; "Isobutylene-based ionomer composites: siliceous filler reinforcement", Polymer 45 (2004) pp. 8091-8096.
Parent J. Scott et al.; "Synthesis and Characterization of Isobutylene-Based Ammonium and Phosphonium Bromide Ionomers", Molecules 2004, 37, pp. 7477-7483.
Vinodh, R., et al.; "Synthesis, Characterization and Antimicrobial Activity of Novel Quaternized Poly (Styrene Ethylene Butylene Poly Styrene)", J Biosci Tech, vol. 1 (1), 2009, pp. 45-51.
Encyclopedia of Polymer Science and Engineering, vol. 4, Composites, Fabrication to Die Design; "Compounding", pp. 66-79.

(Continued)

*Primary Examiner* — Kriellion Sanders
(74) *Attorney, Agent, or Firm* — Jennifer R. Seng (57) ABSTRACT

The invention relates to the use of butyl ionomers or partially halogenated butyl ionomers in reducing a population of and/or preventing accumulation of organisms. The organisms may be bacteria, algae, fungi, mollusca or arthropoda. The invention also relates to coatings for shaped articles comprising the butyl ionomers.

15 Claims, 1 Drawing Sheet

(56) References Cited

OTHER PUBLICATIONS

Ullmann's Encyclopedia of Industrial Chemistry, Fifth, Completely Revised Edition, vol. A23, pp. 288-295, Aug. 26, 2013.
Kaszas G., et al., Synthesis, Bromination and Cure of Isobutylene/Isoprene/P-Methystyrene and Isobutylene/Isoprene/Styrene Terpolymers, Rubber Chem. Technol. 75, 155 (2002) 15 pages (Abstract).

State Intellectual Property Office of P.R.C., Notification of First Office Action and Search Report of Application No. 201080016384.6, mailed Aug. 5, 2013.
Weng et al., Benzoyl chloride modified ionomer films as antimicrobial food packaging materials, International Journal of Food Science & Technology, 32: 229-234. doi: 10.1046/j.1356-2621.1997.00397.x, Abstract.

* cited by examiner

Cell density vs time of DH5α bacterium in the control (containing no elastomer); the base polymer for Example 8; the base polymer for Example 21; Example 8; and Example 21.

BUTYL IONOMERS FOR USE IN REDUCING A POPULATION OF AND/OR PREVENTING ACCUMULATION OF ORGANISMS AND COATINGS MADE THEREFROM

FIELD OF THE INVENTION

The invention relates to the use of butyl ionomers or partially halogenated butyl ionomers exhibiting efficacy in reducing a population of and/or preventing accumulation of organisms. The organisms may be bacteria, algae, fungi, mollusca or arthropoda. The invention also relates to coatings for shaped articles comprising the butyl ionomers.

BACKGROUND

Poly(isobutylene-co-isoprene), or IIR, is a synthetic elastomer commonly known as butyl rubber which has been prepared since the 1940's through the random cationic copolymerization of isobutylene with small amounts of isoprene (1-2 mole %). As a result of its molecular structure, IIR possesses superior air impermeability, a high loss modulus, oxidative stability and extended fatigue resistance.

Butyl rubber is understood to be a copolymer of an isoolefin and one or more, preferably conjugated, multiolefins as co-monomers. Commercial butyl comprises a major portion of isoolefin and a minor amount, not more than 2.5 mol %, of a conjugated multiolefin. Butyl rubber or butyl polymer is generally prepared in a slurry process using methyl chloride as a diluent and a Friedel-Crafts catalyst as part of the polymerization initiator. This process is further described in U.S. Pat. No. 2,356,128 and Ullmann's Encyclopedia of Industrial Chemistry, volume A 23, 1993, pages 288-295.

Halogenation of this butyl rubber produces reactive allylic halide functionality within the elastomer. Conventional butyl rubber halogenation processes are described in, for example, Ullmann's Encyclopedia of Industrial Chemistry (Fifth, Completely Revised Edition, Volume A231 Editors Elvers, et al.) and/or "Rubber Technology" (Third Edition) by Maurice Morton, Chapter 10 (Van Nostrand Reinhold Company© 1987), particularly pp. 297-300.

The presence of allylic halide functionalities allows for nucleophilic alkylation reactions. It has been recently shown that treatment of brominated butyl rubber (BIIR) with nitrogen and/or phosphorus based nucleophiles, in the solid state, leads to the generation of IIR-based ionomers with interesting physical and chemical properties (see: Parent, J. S.; Liskova, A.; Whitney, R. A; Resendes, R. *Journal of Polymer Science, Part A: Polymer Chemistry* 43, 5671-5679, 2005; Parent, J. S.; Liskova, A.; Resendes, R. Polymer 45, 8091-8096, 2004; Parent, J. S.; Penciu, A.; Guillen-Castellanos, S. A.; Liskova, A.; Whitney, R. A. *Macromolecules* 37, 7477-7483, 2004). The ionomer functionality is generated from the reaction of a nitrogen or phosphorous based nucleophile and the allylic halide sites in the BIIR to produce an ammonium or phosphonium ionic group respectively. The physical properties of these BIIR based ionomers (green strength, modulus, filler interactions etc.) are superior to those of their non-ionomeric counterpart.

It has been previously discovered that the addition of para-methylstyrene to the mixed feed of butyl polymerizations (MeCl, IB and IP mixed feed, with $AlCl_3/H_2O$ as initiator) results in a high molecular weight polymer with up to 10 mol % of styrenic groups randomly incorporated along the polymer chain (Kaszas, U.S. Pat. No. 6,960,632; Kaszas et al. Rubber Chemistry and Technology, 2001, 75, 155). The incorporation of para-methylstyrene is found to be uniform throughout the molecular weight distribution due to the similarity in reactivity with isobutylene. The isoprene moieties within the butyl terpolymers can be halogenated by conventional methods leading to similar Type II and Type III allylic halide structures as the current LANXESS halobutyl grades.

CA 2,418,884 and 2,458,741 describe the preparation of butyl-based, peroxide-curable compounds which have high multiolefin content. Specifically, CA 2,418,884 describes the continuous preparation of IIR with isoprene levels ranging from 3 to 8 mol %. Halogenation of this high multiolefin butyl rubber produces a reactive allylic halide functionality within the elastomer. With these elevated levels of isoprene now available, it is possible, in principle, to generate BIIR analogues which contain allylic bromide functionalities ranging from 3 to 8 mol %. Conventional butyl rubber halogenation processes are described in, for example, Ullmann's Encyclopedia of Industrial Chemistry (Fifth, Completely Revised Edition, Volume A231 Editors Elvers, et al.) and/or "Rubber Technology" (Third Edition) by Maurice Morton, Chapter 10 (Van Nostrand Reinhold Company © 1987), particularly pp. 297-300.

Alternatively, a butyl copolymer may comprise a $C_4$-$C_7$ isomonoolefin, such as isobutylene, and a comonomer, such as para-alkylstyrene, preferably para-methylstrene. When halogenated, some of the alkyl substituent groups present in the styrene monomer units contain a benzylic halogen. Additional functional groups can be incorporated by nucleophilic displacement of the benzylic halogen with a variety of nucleophiles as described in U.S. Pat. No. 5,162,445. Use of tertiary amines and phosphines results in the formation of butyl ionomers based on these copolymers with improved physical properties.

There has been continuous effort over the last few decades to develop polymers which inherently possess antibacterial, antifungal and/or antialgal properties by impregnation with an antibacterial, antifungal or antialgal agent. These agents are generally low molecular weight compounds such as antibiotics, phenols, iodine, quaternary ammonium compounds or heavy metals such as silver, tin and mercury. These agents may be attractive, but provide limited protection due to the difficulty in controlling the rate of diffusion of the additive out of the polymer matrix. This leaching eventually renders the material ineffective, possesses a potential environmental risk, and creates the potential for reaction of the leached material with other organic substances. As well, releasing these agents into the environment increases microbial resistance to the agents.

Organic antibacterial, antifungal or antialgal agents have limited incorporability into polymer compositions because, being organic, they typically have a vaporization point less than the temperatures involved during the formation of the polymer compositions. Previous studies have shown that polymeric compounds containing permanently bound antibacterial, antifungal or antialgal agents display advantages over polymeric compounds which contain unbound conventional low molecular weight counterparts. Compounds with conventional agents exhibit better durability with low liberation of toxic products into the environment, thereby reducing losses associated with volatilization, photolytic decomposition, and transportation. Moreover, increased efficiency, selectivity and handling safety are additional benefits that may be realized.

With other polymeric systems in which the antibacterial, antifungal or antialgal agent is bound to the polymer, incorporation of the active material in the polymer is often part of the polymerization process, which can lead to process problems and/or loss of polymer properties. Additionally, the modification of a polymer to incorporate an antibacterial, antifungal or antialgal agent may lead to negative effects on the physical properties of the polymer, rendering the polymer less suitable for its intended application.

Although polymeric compounds containing an antibacterial agent have been prepared and tested, very few examples with adequate antibacterial capabilities have been discovered. In particular, a number of compounds are effective against gram negative bacteria such as *Escherichia coil* and *Salmonella*, but few are also effective against gram positive bacteria such as *Staphylococcus*, *Bacillus*, *Listeria* and *Streptococcus*.

As such, the present invention is directed to the use of butyl ionomers in reducing a population of and/or preventing accumulation of organisms, and coatings for articles made from the butyl ionomers.

SUMMARY OF THE INVENTION

According to an aspect of the present invention, there is provided a use of a butyl ionomer in reducing a population of and/or preventing accumulation of organisms on at least a surface of an article.

According to another aspect of the present invention, there is provided a method of reducing a population of and/or preventing accumulation of organisms on at least a surface of an article, the method comprising providing a butyl ionomer on at least the surface of the article.

According to yet another aspect of the present invention, there is provided a surface coating for an article, the coating comprising a butyl ionomer effective in reducing a population of and/or preventing accumulation of organisms on the surface of the article.

The butyl ionomer may reduce a population of and/or preventing accumulation of organisms associated with bio-fouling, for example bacteria, fungi, algae, mollusca or arthropoda. In particular, the ionomer may be useful in preventing the growth of a bio-film on at least a surface of an article comprising the ionomer. Preventing the growth of a bio-film may comprise preventing the formation of a continuous layer of organisms associated with bio-fouling over greater than 25%, 50% or 75% of the surface of the article. The ionomer may prevent accumulation of organisms by preventing an increase in population of the organisms. The ionomer may prevent accumulation of organisms by impeding attachment of the organisms to the article, particularly the portion or portions of the article comprising the ionomer. The ionomer may reduce the population of the organisms by killing individual organisms (for example, via cell membrane disruption) or by inhibiting reproduction of the organisms (for example, by affecting cellular DNA). A combination of the aforementioned mechanisms may be present simultaneously.

The organisms may comprise bacteria, for example gram negative bacteria, such as *Escherichia coli*, *Pseudomonas aeruginosa*, or gram positive bacteria, such as *Staphylococcus aureus* or *Micrococcus luteus*.

The organisms may comprise fungi, for example *Asperigillus Niger*, *Penicillium pinophilum*, *Aureobasidium pullulan*, or *Chaetomium globosum*.

The organisms may comprise algae, for example *Ulothrix gigas*, *Calothrix membranacea*, *Scenedesmus obliquus*, or *Chlorella* sp.

The organisms may comprise mollusca, for example bivalve mollusks such as *Dreissena polymorpha* (zebra mussels) or *Dreissena rostriformis bugensis* (quagga mussels).

The organisms may comprise arthropoda, for example *Crustacea* sp., such as barnacles.

The ionomer may be provided in an amount sufficient to exhibit one or more of the following: prevention of an increase in the population of gram positive bacteria on the article when incubated in the presence of gram positive bacteria at 30° C. for 7 days; prevention of an increase in the population of gram negative bacteria on the article when incubated in the presence of gram positive bacteria at 30° C. for 7 days; prevention of an increase in the population of fungi on the article when incubated in the presence of fungi at 30° C. for 28 days; or, prevention of an increase in the population of algae on the article when incubated in the presence of algae at 30° C. for 28 days. Alternatively or additionally, the ionomer may be provided in an amount sufficient to exhibit a reduction of a population of gram negative bacteria by at least 50%, 60%, 70%, 80% or 90% when incubated at 30° C. for 24 hours.

The ionomer may comprise a cationic nitrogen based functional group derived from a nitrogen based nucleophile. The nitrogen based nucleophile may comprise an amine. The ionomer may comprise a cationic phosphorous based functional group derived from a phosphorous based nucleophile. The phosphorous based nucleophile may comprise a phosphine. The ionomer may have an ionic content of at least 0.2 mol %, 0.4 mol %, 0.6 mol %, 0.8 mol % or 1.0 mol %.

BRIEF DESCRIPTION OF THE DRAWINGS

Having summarized the invention, preferred embodiments thereof will now be described with reference to the accompanying figures, in which.

DETAILED DESCRIPTION OF THE INVENTION

The present invention provides for a polymer composition comprising, generally, a butyl ionomer or a partially halogenated butyl ionomer formed from reaction of halogenated butyl co-polymers with at least one nitrogen or phosphorous based nucleophile. The terms butyl rubber ionomer, butyl ionomer or partially halogenated butyl ionomer may be referred to collectively herein as "ionomer."

The ionomers of the present invention may be prepared from halogenated butyl co-polymers, particularly butyl rubber co-polymers. Butyl co-polymers are generally derived from at least one isoolefin monomer, at least one multiolefin monomer and optionally further copolymerizable monomers.

In one embodiment, the ionomer may comprise repeating units derived from an isoolefin monomer and a conjugated diene monomer. In another embodiment, the butyl ionomer may comprise repeating units derived from an isoolefin monomer and a styrenic monomer. In yet another embodiment, the butyl ionomer may comprise repeating units derived from an isoolefin monomer, a conjugated diene monomer and a styrenic monomer. In embodiments comprising repeating units derived from a conjugated diene monomer, the number of olefin bonds derived from such units may comprise an elevated amount of at least 2.2 mol %, 3.0 mol %, 4.1 mol %, 5.0 mol %, 6.0 mol %, 7.0 mol %, 7.5 mol %, or 8.0 mol %.

The butyl polymer is not limited to a specific isoolefin. Any isoolefin, as known to those of skill in the art, are contemplated by the present invention including isoolefins having, for examples, within the range of from 4 to 16 carbon atoms.

In one embodiment of the present invention, isoolefins having from 4-7 carbon atoms are contemplated. Examples of isoolefins for use in the present invention include isobutene, 2-methyl-1-butene, 3-methyl-1-butene, 2-methyl-2-butene, 4-methyl-1-pentene and mixtures. A preferred isoolefin is isobutene (isobutylene).

Similarly, the butyl polymer is not limited to a specific multiolefin. Multiolefins copolymerizable with the isoolefins, as known to one skilled in the art, can be used in the practice of the present invention. Conjugated diene multiolefin monomers are preferred. Examples of such multiolefins include, for example, those having in the range of from 4-14 carbon atoms. Examples of suitable multiolefins include isoprene, butadiene, 2-methylbutadiene, 2,4-dimethylbutadiene, piperyline, 3-methyl-1,3-pentadiene, 2,4-hexadiene, 2-neopentylbutadiene, 2-methly-1,5-hexadiene, 2,5-dimethly-2,4-hexadiene, 2-methyl-1,4-pentadiene, 2-methyl-1,6-heptadiene, cyclopentadiene, methylcyclopentadiene, cyclohexadiene, 1-vinyl-cyclohexadiene and mixtures thereof. A preferred multiolefin comprises isoprene.

In another embodiment of the present invention, the butyl co-polymer may further include an additional co-monomer, as known to those of skill in the art, other than the above referenced multiolefins. Co-monomers include monomers copolymerizable with the isoolefins and/or dienes. Co-monomers suitable for use in the present invention include, for example, styrenic monomers, such as alkyl-substituted vinyl aromatic co-monomers, including but not limited to a $C_1$-$C_4$ alkyl substituted styrene. Specific examples of such co-monomers include, for example, α-methyl styrene, p-methyl styrene, chlorostyrene, cyclopentadiene and methylcyclopentadiene. In this embodiment of the present invention, the butyl polymer may include, for example, random copolymers of isobutylene, isoprene and para-methylstryene.

In yet another embodiment of the present invention, an isoolefin monomer, as described above, is polymerized with a styrenic monomer, for example an alkyl-substituted vinyl aromatic co-monomer, including but not limited to a $C_1$-$C_4$ alkyl substituted styrene. Specific examples of styrenic monomers include, for example, α-methyl styrene, p-methyl styrene, chlorostyrene, cyclopentadiene and methylcyclopentadiene. In this embodiment, the butyl polymer may include, for example, random copolymers of isobutylene and para-methylstryene.

Butyl polymers, as described above, are formed from a mixture of monomers described herein. In one embodiment, the monomer mixture comprises from about 80% to about 99% by weight of an isoolefin monomer and from about 1% to 20% by weight of a multiolefin monomer. In another embodiment, the monomer mixture comprises from about 85% to about 99% by weight of an isoolefin monomer and from about 1% to 15% by weight of a multiolefin monomer. In certain embodiments of the present invention three monomers may be employed. In these embodiments, the monomer mixture comprises about 80% to about 99% by weight of isoolefin monomer, from about 0.5% to about 5% by weight of a multiolefin monomer and from about 0.5% to about 15% by weight a third monomer copolymerizable with the isoolefin or multiolefin monomer. In one embodiment, the monomer mixture comprises from about 85% to about 99% by weight of an isoolefin monomer, from about 0.5% to about 5% by weight of a multiolefin monomer and from about 0.5% to about 10% by weight of a third monomer copolymerizable with the isoolefin or multiolefin monomers. In yet another embodiment, the monomer mixture comprises from about 80% to about 99% by weight of an isoolefin monomer and from about 1% to 20% by weight of a styrenic monomer.

Once the butyl polymer is formed from the monomer mixture, the butyl polymer may be subjected to a halogenation process in order to form the halogenated butyl polymer or halobutyl polymer. Bromination or chlorination can be performed according to the process known by those skilled in the art as in, for example, the procedures described in Rubber Technology, 3rd Ed., Edited by Maurice Morton, Kluwer Academic Publishers, pp. 297-300 and further documents cited therein.

In one embodiment of the present invention, the ionomers may be prepared from a halogenated butyl polymer having from 0.5 to 2.2 mol % of the multiolefin monomer. For example, a halogenated butyl for use in the present invention includes a halogenated butyl having isobutylene and less than 2.2 mole percent isoprene which is commercially available from LANXESS Deutschland GmbH and sold under the name BB2030. In another embodiment of the present invention, the ionomers may be prepared from a halogenated butyl polymer having a higher multiolefin content, for example greater than 2.5 mol %. In yet another embodiment, the ionomers may be prepared from a halogenated butyl polymer having a multiolefin content of greater than 3.5 mol %. In still another embodiment, the multiolefin content of the halogenated butyl polymer is greater than 4.0 mol %. In even another embodiment, the multiolefin content of the halogenated butyl polymer is greater than 7.0 mol %. The preparation of a suitable high multiolefin butyl rubber polymer, for use in the present invention, is described in co-pending application CA 2,418,884, which is incorporated herein by reference.

During halogenation of a butyl polymer containing conjugated dienes, such as isoprene, some or all of the multiolefin content of the butyl polymer is converted to allylic halides. The total allylic halide content of the halobutyl polymer may not exceed the starting multiolefin content of the parent butyl polymer. The allylic halide sites allow for reacting with and attaching a nucleophile to the halobutyl polymer. For halobutyl polymers containing no allylic halides, for example, halobutyl polymers derived from isobutylene and styrenic monomers, benzylic halides, formed by halogenation of the styrenic monomer, may be reacted to form the ionomer rather than allylic halides. The same logic would therefore apply to benzylic halides as allylic halides; the total amount of ionomeric moieties cannot exceed the available amount of benzylic halides.

In one embodiment of the present invention, the allylic halide or benzylic halide sites of the halobutyl polymer are reacted with at least one nitrogen or phosphorus containing nucleophile having the following formula, wherein, A is a nitrogen or phosphorus; and, $R_1$, $R_2$ and $R_3$ are selected from the group consisting of linear or branched $C_1$-$C_{15}$ alkyl substituents, an aryl substituent which is monocyclic or composed of fused $C_4$-$C_8$ rings, and/or a hetero atom selected from, for example, B, N, O, Si, P, and S.

Nucleophiles for use in the present invention include, for examples, those nucleophiles having at least one neutral nitrogen or phosphorus center which possesses a lone pair of electrons that are electronically and sterically accessible for participation in nucleophilic substitution reactions. Suitable nucleophiles, for use in the present invention include, for examples, trimethylamine, triethylamine, triisopropylamine, tri-n-butylamine, trimethylphosphine, triethylphosphine, triisopropylphosphine, tri-n-butylphosphine, triphenylphosphine 2-dimethylaminoethanol, 1-dimethylamino-2-propanol, 2-(isopropylamino)ethanol, 3-dimethylamino-1-propanol, N-methyldiethanolamine, 2-(diethylamino) ethanol, 2-dimethylamino-2-methyl-1-propanol, 2-[2-(dimethylamino)ethoxy]ethanol, 4-(dimethylamino)-1-butanol, N-ethyldiethanolamine, triethanolamine, 3-diethylamino-1-propanol, 3-(diethylamino)-1,2-propanediol, 2-{[2-(dimethylamino)ethyl] methylamino}ethanol, 4-diethylamino-2-butyn-1-ol, 2-(diisopropylamino)ethanol, N-butyldiethanolamine, N-tert-butyldiethanolamine, 2-(methylphenylamino)ethanol, 3-(dimethylamino)benzyl alcohol, 2-[4-(dimethylamino) phenyl]ethanol, 2-(N-ethylanilino)ethanol, N-benzyl-N-methylethanolamine, N-phenyldiethanolamine, 2-(dibutylamino)ethanol, 2-(N-ethyl-N-m-toluidino)ethanol, 2,2'-(4-methylphenylimino)diethanol, tris[2-(2-methoxyethoxy) ethyl]amine, 3-(dibenzylamino)-1-propanol and mixtures thereof.

In one embodiment of the present invention, the amount of nucleophile reacted with the butyl polymer may be in the range of from 0.05 to 5 molar equivalents. In another embodiment, the amount of nucleophile reacted with the butyl polymer may be in the range of from 0.5 to 4 molar equivalents. In yet another embodiment, the ratio of nucleophile reacted with the butyl polymer is 1 to 3 molar equivalents. The ratios of nucleophile to butyl polymer are based on the total molar amount of allylic halide or benzylic halide present in the halobutyl polymer.

As stated above, the nucleophile reacts with the allylic or benzylic halide functionality of the halobutyl polymer resulting in units of ionomeric moieties where the allylic or benzylic halide functionality existed on the halobutyl polymer. The total content of ionomeric moiety in the butyl ionomer may not exceed the starting amount of allylic or benzylic halide in the halobutyl polymer; however, residual allylic halides, benzylic halides and/or residual multiolefins may be present. In embodiments of the present invention where substantially all of the allylic or benzylic halides sites are reacted with the nucleophile, a butyl ionomer is formed. In embodiments where less than all the allylic or benzylic halide sites are reacted with the nucleophile, a partially halogenated butyl ionomer is formed.

In one embodiment of the present invention, the resulting ionomer possesses an ionic content of at least 0.5 mol % of the ionomeric moiety. In another embodiment, the ionomer possesses an ionic content of at least 0.75 mol % of the ionomeric moiety. In yet another embodiment, the ionomer possesses an ionic content of at least 1.0 mol % of the ionomeric moiety. In yet another embodiment, the ionomer possesses an ionic content of at least 1.5 mol % of the ionomeric moiety.

In some cases, residual allylic halides may be present in an amount of from 0.1 mol % up to an amount not exceeding the original allylic halide content of the halobutyl polymer used to produce the butyl ionomer. In other embodiments, residual multiolefin may be present in an amount of from 0.1 mol % up to an amount not exceeding the original multiolefin content of the butyl polymer used to produce the halobutyl polymer. In one embodiment, the residual multiolefin content of the ionomer is at least 0.2 mol %. In another embodiment, the residual multiolefin content of the ionomer is at least 0.6 mol %. In yet another embodiment, the residual multiolefin content of the ionomer is least 0.8 mol %. In yet another embodiment, the residual multiolefin content of the ionomer is least 1.0 mol %.

In yet another embodiment, the residual multiolefin content of the ionomer is at least 2.0 mol %. In yet another embodiment, the residual multiolefin content of the ionomer is least 3.0 mol %. In yet another embodiment, the residual multiolefin content of the ionomer is at least 4.0 mol %.

In one embodiment of the present invention, the ionomer may comprise repeating units derived from at least one isoolefin monomer, at least 0.5% of repeating units derived from at least one multiolefin monomer, and at least one nitrogen or phosphorous based nucleophile, wherein the butyl ionomer or partially halogenated butyl ionomer is formed by preparing a monomer mixture comprising the isoolefin and a multiolefin, reacting the monomer mixture to form a polymer, halogenating the polymer to form halo functional sites on the polymer, and reacting the halo functional sites with the nucleophile.

The polymer composition, according to the present invention, may include one or more fillers. Suitable fillers for use in the present invention are composed of particles of a mineral, such as, for example, silica, silicates, clay (such as bentonite), gypsum, alumina, titanium dioxide, talc and the like, as well as mixtures thereof.

Further examples of suitable fillers include:

highly dispersable silicas, prepared e.g. by the precipitation of silicate solutions or the flame hydrolysis of silicon halides, with specific surface areas of 5 to 1000, preferably 20 to 400 $m^2/g$ (BET specific surface area), and with primary particle sizes of 10 to 400 nm; the silicas can optionally also be present as mixed oxides with other metal oxides such as Al, Mg, Ca, Ba, Zn, Zr and Ti;

synthetic silicates, such as aluminum silicate and alkaline earth metal silicate;

magnesium silicate or calcium silicate, with BET specific surface areas of 20 to 400 $m^2/g$ and primary particle diameters of 10 to 400 nm;

natural silicates, such as kaolin and other naturally occurring silica;

natural clays, such as montmorillonite and other naturally occurring clays;

organophilically modified clays such as organophilically modified montmorillonite clays (e.g. Cloisite® Nanoclays available from Southern Clay Products) and other organophilically modified naturally occurring clays;

glass fibers and glass fiber products (matting, extrudates) or glass microspheres;

metal oxides, such as zinc oxide, calcium oxide, magnesium oxide and aluminum oxide;

metal carbonates, such as magnesium carbonate, calcium carbonate and zinc carbonate;

metal hydroxides, e.g. aluminum hydroxide and magnesium hydroxide or combinations thereof.

In one embodiment of the present invention, the mineral filler is silica. In another embodiment the mineral filler is silica prepared by the carbon dioxide precipitation of sodium silicate.

Dried amorphous silica particles suitable for use as mineral fillers in accordance with the present invention may have a mean agglomerate particle size in the range of from 1 to 100 microns. In one embodiment of the present invention, the dried amorphous silica particles have a mean agglomerate particle size in the range of from 10 and 50 microns. In another embodiment of the present invention, the dried amorphous silica particles have a mean agglomerate particle size in the range of from between 10 and 25 microns. In one embodiment of the present invention, it is contemplated that less than 10 percent by volume of the agglomerate particles are below 5 microns or over 50 microns in size. Suitable amorphous dried silica has, for example, a BET surface area, measured in accordance with DIN (Deutsche Industrie Norm) 66131, of between 50 and 450 square meters per gram and a DBP absorption, as measured in accordance with DIN 53601, of between 150 and 400 grams per 100 grams of silica, and a drying loss, as measured according to DIN ISO 787/11, of from 0 to 10 percent by weight. Suitable silica fillers are commercially sold under the names HiSil 210, HiSil 233 and HiSil 243 available from PPG Industries Inc. Also suitable are Vulkasil S and Vulkasil N, commercially available from Bayer AG.

Mineral fillers, as used in the present invention, can also be used alone or in combination with known non-mineral fillers, such as:
  carbon blacks; suitable carbon blacks are preferably prepared by the lamp black, furnace black or gas black process and have BET specific surface areas of 20 to 200 $m^2/g$, for example, SAF, ISAF, HAF, FEF or GPF carbon blacks; or
  rubber gels, preferably those based on polybutadiene, butadiene/styrene copolymers, butadiene/acrylonitrile copolymers and polychloroprene.

High aspect ratio fillers useful in the present invention include clays, talcs, micas, etc. with an aspect ratio of at least 1:3. The fillers may include a circular or nonisometric materials with a platy or needle-like structure. The aspect ratio is defined as the ratio of mean diameter of a circle of the same area as the face of the plate to the mean thickness of the plate. The aspect ratio for needle and fiber shaped fillers is the ratio of length to diameter. In one embodiment of the present invention, high aspect ratio fillers have an aspect ratio of at least 1:5. In another embodiment of the present invention, high aspect ratio fillers have an aspect ratio at least 1:7. Yet in another embodiment, high aspect ratio fillers have an aspect ratio 1:7 to 1:200. Fillers in accordance with the present invention may have, for example, a mean particle size in the range of from 0.001 to 100 microns In anther embodiment, fillers have a mean particle size in the range of from 0.005 and 50 microns. In another embodiment, fillers have a mean particle size in the range of from 0.01 and 10 microns. A suitable filler may have a BET surface area, measured in accordance with DIN (Deutsche Industrie Norm) 66131, of between 5 and 200 square meters per gram.

In one embodiment of the present invention, high aspect ratio fillers comprises a nanoclay, such as, for example, an organically modified nanoclay. The present invention is not limited to a specific nanoclay; however, natural powdered smectite clays, such as sodium or calcium montmorillonite, or synthetic clays such as hydrotalcite and laponite are suitable examples as starting materials. In one embodiment, the high aspect fillers include organically modified montmorillonite nanoclays. The clays may be modified by substitution of the transition metal for an onium ion, as is known in the art, to provide surfactant functionality to the clay that aids in the dispersion of the clay within the generally hydrophobic polymer environment. In one embodiment of the present invention, onium ions are phosphorus based (e.g.: phosphonium ions) and nitrogen based (e.g.: ammonium ions) and contain functional groups having from 2 to 20 carbon atoms (e.g.: $NR_4^{+-}MMT$).

The clays may be provided, for example, in nanometer scale particle sizes, such as, less than 25 μm by volume. In one embodiment, the particle size is in the range of from 1 to 50 μm. In another embodiment, the particle size is in the range of from 1 to 30 μm. In yet another embodiment, the particle size is in the range of from 2 to 20 μm.

In addition to silica, the nanoclays may also contain some fraction of alumina. In one embodiment, the nanoclays may contain from 0.1 to 10 wt % alumina. In another embodiment the nanoclays may contain from 0.5 to 5 wt % alumina. In yet anther embodiment, the nanoclays may contain from 1 to 3 wt % alumina.

Examples of commercially available organically modified nanoclays suitable for use in the present invention as high aspect ratio fillers include, for example, those sold under the trade name Cloisite® clays 10A, 20A, 6A, 15A, 30B, or 25A. In one embodiment, the high aspect ratio fillers may be added to the pre-formed butyl ionomer to form a nanocomposite in an amount of from 3 to 80 phr. In another embodiment, the amount of high aspect ratio fillers in the nanocomposite is from 5 to 30 phr. In yet another embodiment, the amount of high aspect ratio fillers in the nanocomposite is from 5 to 15 phr.

The ionomer may be cured or uncured. When cured, the ionomer may comprise components derived from a curing system. The choice of curing system suitable for use is not particularly restricted and is within the purview of a person skilled in the art. In certain embodiments of the present invention, curing system may be sulphur-based or peroxide-based. A typical sulfur-based curing system comprises: (i) a metal oxide, (ii) elemental sulfur and (iii) at least one sulfur-based accelerator. The use of metal oxides as a component in the curing system is well known in the art. A suitable metal oxide is zinc oxide, which may be used in the amount of from about 1 to about 10. In another embodiment of the present invention, the zinc oxide may be used in an amount of from about 2 to about 5, parts by weight per hundred parts by weight butyl polymer in the nanocomposite. Elemental sulfur, comprising component (ii) of the preferred curing system is typically used in amounts of from about 0.2 to about 2 parts by weight, per hundred parts by weight butyl polymer in the composition. Suitable sulfur-based accelerators (component (iii) of the preferred curing system) may be used in amounts of from about 0.5 to about 3 parts by weight, per hundred parts by weight butyl polymer in the composition. Non-limiting examples of useful sulfur-based accelerators may be selected from the thiuram sulfides such as tetramethyl thiuram disulfide (TMTD), the thiocarbamates such as zinc dimethyl dithiocarbamate (ZDC) and the thiazyl and benzothiazyl compounds such as mercaptobenzothiazyl disulfide (MBTS). In one embodiment of the present invention, the sulphur based accelerator is mercaptobenzothiazyl disulfide.

Peroxide based curing systems may also be suitable for use in the present invention. For example, a peroxide-based curing system may comprises a peroxide curing agent, for example, dicumyl peroxide, di-tert-butyl peroxide, benzoyl peroxide, 2,2'-bis(tert.-butylperoxy diisopropylbenzene (Vulcup® 40KE), benzoyl peroxide, 2,5-dimethyl-2,5-di(tert-butylperoxy)-hexyne-3, 2,5-dimethyl-2,5-di(benzoylperoxy)hexane, (2,5-bis(tert.-butylperoxy)-2,5-dimethyl hexane and the like. One such peroxide curing agent comprises dicumyl peroxide and is commercially available under the name DiCup 40C. In one embodiment, the peroxide curing agent is used in an amount of 0.2 to 7 parts per hundred parts of rubber (phr) In another embodiment, the peroxide curing agent is used in an amount of 1 to 6 phr. In yet another embodiment, the peroxide curing agent is used in an amount of about 4 phr. Peroxide curing co-agents can also be used in the present invention. Suitable peroxide curing co-agents include, for example, triallyl isocyanurate (TAIC), commercially available under the name DIAK 7 from DuPont Or N,N'-m-phenylene dimaleimide know as HVA-2 (DuPont Dow), triallyl cyanurate (TAC) or liquid polybutadiene known as Ricon D 153 (supplied by Ricon Resins). Peroxide curing co-agents may be used in amounts equivalent to those of the peroxide curing agent, or less.

In some embodiments of the present invention, stabilizers, anti-oxidants, tackifiers, and/or other additives as known to those of skill in the art may also be added in the usual way and in the normal amounts for compounding the butyl ionomers of the present invention.

In embodiments where the polymer composition includes the ionomer, fillers, curing agents, and/or other additives, the ingredients may be compounded together using conventional compounding techniques. Suitable compounding techniques include, for example, mixing the ingredients of the composite together using, for example, an internal mixer, such as a Banbury mixer, a miniature internal mixer, such as a Haake or Brabender mixer, or a two roll mill mixer. An extruder also provides good mixing, and permits shorter mixing times. It is possible to carry out the mixing in two or more stages, and the mixing can be done in different apparatus, for example one stage in an internal mixer and one stage in an extruder. For further information on compounding techniques, see Encyclopedia of Polymer Science and Engineering, Vol. 4, p. 66 et seq. (Compounding). Other techniques, as known to those of skill in the art, are further suitable for compounding.

In one embodiment of the present invention, the ionomer may be formed into a shaped article or applied to an existing article. The article may be made entirely from the ionomer. Alternatively, a portion of the article may comprise the ionomer. The ionomer may be provided on the surface of the article only. The ionomer may be integrally molded into the surface or attached to the surface, for example adhesively or via fasteners. The ionomer may be provided as part of a composite material comprising a plastic. The plastic may comprise polyethylene, polypropylene, an EP polymer, an EPDM polymer, or a nylon polymer. The composite material may comprise a thermoplastic vulcanizate comprising the butyl ionomer and the plastic material.

The ionomer may be provided as a surface coating for the article. The surface coating may comprise a paint. The surface coating may be in the form of an applied membrane (of any suitable thickness), a chemical vapour deposit, or a powder coating. The coating may further comprise a plastic.

The ionomer may be provided, as part of a coating or otherwise, with the proviso that no additionally added antibacterial, antifungal or antialgal agents are present, particularly such agents that could leach out of the coating. The coating may consist essentially of the ionomer, which is meant to include any fillers or curative agents that may be present as part of the ionomer.

The article may comprise: a fluid conduit, such as a hose or pipe; a container, such as a bottle, tote, storage tank, etc.; a container closure or lid; a seal or sealant, such as a gasket or caulking; a material handling apparatus, such as an auger or conveyor belt; a marine vessel or structure, such as a ship, dock, or oil drilling platform; a cooling tower; a metal working apparatus, or any apparatus in contact with metal working fluids; an engine component, such as fuel lines, fuel filters, fuel storage tanks, gaskets, seals, etc.; a membrane, for fluid filtration or tank sealing; or, footwear, particularly portions of footwear that come into direct contact with the foot.

Additional examples where the butyl ionomers may be used in articles or coatings include, but are not limited to, the following: appliances, baby products, bathroom fixtures, bathroom safety, flooring, food storage, garden, kitchen fixtures, kitchen products, office products, pet products, sealants and grouts, spas, water filtration and storage, equipment, food preparation surfaces and equipments, shopping carts, surface applications, storage containers, footwear, protective wear, sporting gear, carts, dental equipment, door knobs, clothing, telephones, toys, catheterized fluids in hospitals, surfaces of vessels and pipes, coatings, food processing, biomedical devices, filters, additives, computers, ship hulls, shower walls, tubing to minimize the problems of biofouling, pacemakers, implants, wound dressing, medical textiles, ice machines, water coolers, fruit juice dispensers, soft drink machines, piping, storage vessels, metering systems, valves, fittings, attachments, filter housings, linings, and barrier coatings.

In one aspect of the invention, the ionomer exhibits antibacterial, antifungal and/or antialgal properties. This feature of the ionomer is believed to be a result of the ionic nature of the formed ionomer. Although the inventors do not intend to be bound by theory, it is believe that the ionic feature of the ionomer imparts antibacterial, antifungal and/or antialgal properties not observed in typical halogenated butyl polymer.

As discussed above, antibacterial, antifungal and/or antialgal additives may be attractive, but are limited in that their protection is often short-lived due to difficulties in controlling the rate of diffusion of the antibacterial, antifungal and/or antialgal additive out of the polymer matrix. This leaching of the additives out of the polymer matrix eventually renders the material ineffective. In addition, leaching creates a potential environmental risk and a risk of reaction of the leached material with other organic substances. Having the ionic group covalently bound to the polymer backbone, as in the ionomers of the present invention, eliminates additive leaching issues, as well as potentially increasing anti-microbial efficacy, selectivity and handling safety of the polymer.

The ionomer described herein is advantageous as one has the ability to post modify a preexisting polymer allowing for control over the polydispersity, molecular weight and polymer topology, which can sometimes be affected when antibacterial, antifungal or antialgal agents are added during polymerization. The ionomers described herein not only retain the properties of the original polymer, but also exhibits enhanced physical properties, such as improved filler interaction, adhesion, and green strength. These properties are useful in the formation of shaped articles and adhesively applied coatings.

The present invention is particularly useful against microorganisms. By way of example, the following microorganisms are mentioned without imposing any limitation to the types microorganism in which the properties of the instant butyl ionomer are effective:

Algae: *chlorophyta, rhodophyta, glaucophyta, chlorarachniophytes, euglenids, heterokonts, haptophyta, cryptomonads, dinoflagellates*

Fungii: *Alternaria, aspergillus, basidiomycetes, botrytis, candida albicans, cephalosporium, chaetomium, cladosporium; curvularia, drechslera, epicoccum, fusarium, geotrichum, helminthosporium; humicola; monilia, neuspora, nigrospora, penicillium, phoma, pullularia, rhizophus, rhodotorula, scopulariopsis, stemphylium, trichoderma, unocladium* and *verticillium*

Gram-negative bacteria—*Salmonella, Shigella, Neisseria gonorrhoeae, Neisseria meningitidis, Haemophilus influenzae, Escherichia coli, Klebsiella, Pseudomonas aeruginosa.*

Gram-positive bacteria—*Bacillus, Listeria, Staphylococcus, Streptococcus, Enterococcus, Clostridium, Epulopiscium, Sarcina, Mycoplasma, Spiroplasma, Ureaplasma, Lactobacillus, Corynebacterium, Propionibacterium, Gardnerella, Frankia, Streptomyces, Actinomyces,* and *Nocardia.*

The ionomer according to the present invention may further be used in cured and uncured polymer compositions, thermoplastic elastomeric compositions, re-moldable polymer compositions, coatings and the like.

Whereas particular embodiments of this invention have been described above for purposes of illustration, it will be evident to those skilled in the art the numerous variations of the details of the present invention may be made without departing from the invention as defined in the appended claims.

The following examples will be used to illustrate particular embodiments of the invention.

Example 1

356 g of LANXESS BB2030 and 16.7 g (1.2 molar equivalents based on allylic bromide content) of triphenylphosphine (TPP) were premixed on a 6"×12" mill at room temperature for 3 minutes. The mixture was then passed through a twin screw extruder at 160° C. Analysis of the final product by $^1$H NMR confirmed the complete conversion of all the allylic bromide of BB2030 to the corresponding ionomeric species with an ionic content of 0.8 mol %. The sample was molded at 100° C. for 5 minutes and its resistance to the growth of gram positive (*Staphylococcus aureus*) was tested in triplicate. The samples were placed on Sab Dex agar (SDA) plates where approximately $10^6$ cells were added, plated and incubated at 30° C. After 7 days, no bacterial growth was observed on the sample, demonstrating the inhibition of butyl-based phosphonium ionomer with 0.8 mol % ionic functionality to the growth of gram positive bacteria.

Example 2

The resistance of the ionomer formed in Example 1 to gram negative bacteria (*Escherichia coli*) was tested using the same procedure as outlined in Example 1. After 7 days, no bacterial growth was observed on the sample, demonstrating the inhibition of butyl-based phosphonium ionomer with 0.8 mol % ionic functionality to the growth of gram negative bacteria.

Example 3

The resistance of the ionomer formed in Example 1 to a combination of gram positive bacteria (*Staphylococcus aureus* and *micrococcus luteus*) was tested using the same procedure as outlined in Example 1. After 7 days, no bacterial growth was observed on the sample, demonstrating the inhibition of butyl-based phosphonium ionomer with 0.8 mol % ionic functionality to the growth of a variety of gram positive bacteria.

Example 4

The resistance of the ionomer formed in Example 1 to a combination of gram negative bacteria (*Escherichia coli* and *Pseudomonas aeruginosa*) was tested using the same procedure as outlined in Example 1. After 7 days, no bacterial growth was observed on the sample, demonstrating the inhibition of butyl-based phosphonium ionomer with 0.8 mol % ionic functionality to the growth of a variety of gram negative bacteria.

Example 5

The resistance of the ionomer formed in Example 1 to the fungus *Asperigillus Niger* was tested in triplicate. The samples were placed on Malt agar plate, followed by the addition of approximately $10^6$ spores of *Aspergillus Niger* to the sample, plated and incubated at 30° C. After 28 days, no mold growth was observed on the sample, demonstrating the antifungal nature of a butyl-based phosphonium ionomer with 0.8 mol % ionic functionality.

Example 6

The resistance of the ionomer formed in Example 1 to a cocktail of fungi was tested in triplicate. The samples were placed on Malt agar plate, followed by the addition of approximately $10^6$ spores of a cocktail of *Aspergillus niger, Penicillium pinophilum, Aureobasidium pullulan*, and *Chaetomium globosum* to the sample, plated and incubated at 30° C. After 28 days, no mold growth was observed on the sample, demonstrating the antifungal nature of the butyl-based phosphonium ionomer with 0.8 mol % ionic functionality to a wide variety of fungi.

Example 7

The resistance of the ionomer formed in Example 1 to a cocktail of algae was tested in triplicate. The samples were placed on Malt agar plate, followed by the addition of approximately $10^6$ concentration of a cocktail of *Ulothrix gigas, Calothrix membranacea, Scenedesmus obliquus*, and *Chlorella* sp. to the sample, plated and incubated at 30° C. After 28 days, no algae growth was observed on the sample, demonstrating the antialgal nature of the butyl-based phosphonium ionomer with 0.8 mol % ionic functionality to a wide variety of algae.

Example 8

Figure 1:
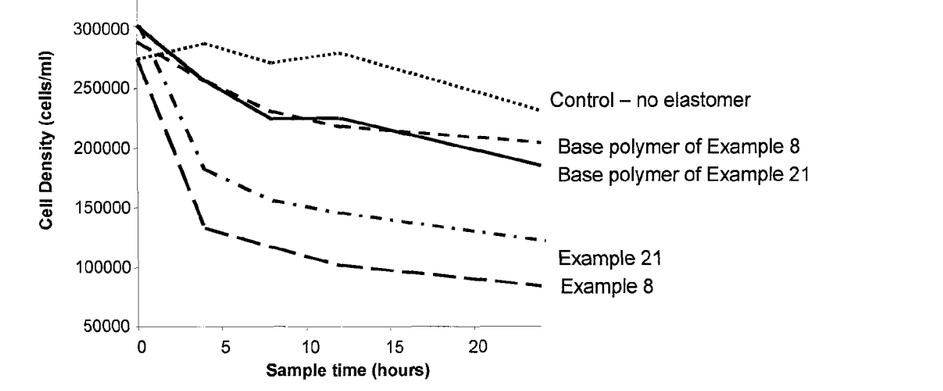
FIG. 1 shows a plot of cell density versus time, illustrating a reduction in the population of organisms on a butyl ionomer surface.

Approximately 1 g of Example 1 was dipped in 95% ethanol for sterilization and then placed into a 20 mL Scintillation vial where 10 mL of M9 media was added. A colony of DH5α bacteria (a strain of *E. Coli* gram negative bacteria) was selected and suspended into M9 media salt solution. Next, 500 µL aliquots of the DH5α bacterium suspension were added to each tube. A rubber-less treatment was used as a control and 495 µL samples were tested at 0, 4, 8, 10 and 24 hours. Bacterium counts were generated using flow cytometry and nucleic acid stain SYBER Green® using the following procedure: 5 µLt of 100× SYBER Green® dye (suspended in DMSO) was added to 495 µL of sample, for a final SYBER Green® concentration of 1×. The samples were incubated in the dark for approximately 15 minutes and then run on the flow cytometer. The percentage of dead cells was measured using flow cytometry and the nucleic acid stain SYTOX® after 24 hours. Over 60% of the bacteria were killed demonstrating the biocidal nature of the butyl-based phosphonium ionomer with 0.8 mol % ionic functionality. See FIG. 1.

Example 9

277 g of LANXESS BB2030 and 2.19 g (0.2 molar equivalents based on allylic bromide content) of triphenylphosphine (TPP) were premixed on a 6"×12" mill at room temperature for 3 minutes. The mixture was then passed through a twin screw extruder at 160° C. Analysis of the final product by $^1$H NMR confirmed the presence of 0.2 mol % phosphonium ionic groups. The sample was molded at 100° C. for 5 minutes and its resistance to a cocktail of gram positive bacteria (*Staphylococcus aureus* and *Micrococcus luteus*) was tested in

Example 10

The resistance of the ionomer formed in Example 9 to a cocktail of gram negative bacteria (*Escherichia coli* and *Pseudomonas aeruginosa*) was tested using the same procedure as outlined in Example 9. After 7 days, no bacterial growth was observed on the sample, demonstrating the inhibition of butyl-based phosphonium ionomer with 0.2 mol % ionic functionality to the growth of a variety of gram negative bacteria.

Example 11

The resistance of the ionomer formed in Example 9 to a cocktail of fungi was tested in triplicate. The samples were placed on Malt agar plate, followed by the addition of approximately $10^6$ spores of a cocktail of *Aspergillus niger*, *Penicillium pinophilum*, *Aureobasidium pullulan*, and *Chaetomium globosum* to the sample, plated and incubated at 30° C. After 28 days, no mold growth was observed on the sample, demonstrating the antifungal nature of the butyl-based phosphonium ionomer with 0.2 mol % ionic functionality to a wide variety of fungi.

Example 13

273 g of LANXESS BB2030 and $6.47_g$ (0.6 molar equivalents based on allylic bromide content) of triphenylphosphine (TPP) were premixed on a 6"×12" mill at room temperature for 3 minutes. The mixture was then passed through a twin screw extruder at 160° C. Analysis of the final product by $^1$H NMR confirmed the presence of 0.6 mol % phosphonium ionic groups. The sample was molded at 100° C. for 5 minutes and its resistance to a cocktail of gram positive bacteria (*Staphylococcus aureus* and *Micrococcus luteus*) was tested in triplicate. The samples were placed on Sab Dex agar (SDA) plates where approximately $10^6$ cells were added, plated and incubated at 30° C. After 7 days, no bacterial growth was observed on the sample, demonstrating the inhibition of butyl-based phosphonium ionomer with 0.6 mol % ionic functionality to the growth of a variety of gram positive bacteria.

Example 14

The resistance of the ionomer formed in Example 13 to a cocktail of gram negative bacteria (*Escherichia coli* and *Pseudomonas aeruginosa*) was tested using the same procedure as outlined in Example 9. After 7 days, no bacterial growth was observed on the sample, demonstrating the inhibition of butyl-based phosphonium ionomer with 0.6 mol % ionic functionality to the growth of a variety of gram negative bacteria.

Example 15

The resistance of the ionomer formed in Example 13 to a cocktail of fungi was tested in triplicate. The samples were placed on Malt agar plate, followed by the addition of approximately $10^6$ spores of a cocktail of *Aspergillus niger*, *Penicillium pinophilum*, *Aureobasidium pullulan*, and *Chaetomium globosum* to the sample, plated and incubated at 30° C. After 28 days, no mold growth was observed on the sample, demonstrating the antifungal nature of the butyl-based phosphonium ionomer with 0.6 mol % ionic functionality to a wide variety of fungi.

Example 16

The resistance of the ionomer formed in Example 13 to a cocktail of algae was tested in triplicate. The samples were placed on Malt agar plate, followed by the addition of approximately $10^6$ concentration of a cocktail of *Ulothrix gigas*, *Calothrix membranacea*, *Scenedesmus obliquus*, and *Chlorella* sp. to the sample, plated and incubated at 30° C. After 28 days, no algae growth was observed on the sample, demonstrating the antialgal nature of the butyl-based phosphonium ionomer with 0.6 mol % ionic functionality to a wide variety of algae.

Example 17

LANXESS BB2030 was passed through a twin screw extruder at 160° C. where N,N-dimethylaminoethanol (DMAE) was added at a rate of 0.4 mL/min. Analysis of the final product by $^1$H NMR confirmed the presence of 0.8 mol % ammonium ionic groups. The sample was molded at 100° C. for 5 minutes and its resistance to gram positive bacteria (*Staphylococcus aureus*) was tested in triplicate. The samples were placed on Sab Dex agar (SDA) plates where approximately $10^6$ cells were added, plated and incubated at 30° C. After 7 days, no bacterial growth was observed on the sample, demonstrating the inhibition of butyl-based ammonium ionomer with 0.8 mol % ionic functionality to the growth of gram positive bacteria.

Example 18

The resistance of the ionomer formed in Example 17 to gram negative bacteria (*Escherichia coli*) was tested using the same procedure as outlined in Example 17. After 7 days, no bacterial growth was observed on the sample, demonstrating the inhibition of butyl-based ammonium ionomer with 0.8 mol % ionic functionality to the growth of gram negative bacteria.

Example 19

US 2007/0218296 A1, which is incorporated herein by reference, describes the preparation of high isoprene BIIR. 204 g of brominated high isoprene butyl and 8.04 g (1.2 molar equivalents based on allylic bromide content of the brominated high isoprene BIIR) of triphenylphosphine (TPP) were premixed on a 6"×12" mill at room temperature for 3 minutes. The mixture was then passed through a twin screw extruder at 160° C. Analysis of the final product by $^1$H NMR confirmed the complete conversion of the allylic bromide to the corresponding ionomeric species with an ionic content of 0.8 mol %. The sample was molded at 100° C. for 5 minutes and its resistance to the growth of gram positive (*Staphylococcus aureus*) was tested in triplicate. The samples were placed on Sab Dex agar (SDA) plates where approximately $10^6$ cells were added, plated and incubated at 30° C. After 7 days, no bacterial growth was observed on the sample, demonstrating the inhibition of high isoprene butyl-based phosphonium ionomer with 0.8 mol % ionic functionality to the growth of gram positive bacteria.

Example 20

The resistance of the ionomer formed in Example 19 to gram negative bacteria (*Escherichia coli*) was tested using the same procedure as outlined in Example 19. After 7 days, no bacterial growth was observed on the sample, demonstrating the inhibition of high isoprene butyl-based phosphonium ionomer with 0.8 mol % ionic functionality to the growth of gram negative bacteria.

Example 21

Approximately 1 g of Example 19 was dipped in 95% ethanol for sterilization and then placed into a 20 mL Scintillation vial where 10 mL of M9 media was added. A colony of DH5α bacteria (a strain of *E. Coli* gram negative bacteria) was selected and suspended into M9 media salt solution. Next, 500 µL aliquots of the DH5α bacterium suspension were added to each tube. A rubber-less treatment was used as a control and 495 µL samples were tested at 0, 4, 8, 10 and 24 hours. Bacterium counts were generated using flow cytometry and nucleic acid stain SYBER Green® using the following procedure: 5 µL of 100× SYBER Green® dye (suspended in DMSO) was added to 495 µL of sample, for a final SYBER Green® concentration of 1×. The samples were incubated in the dark for approximately 15 minutes and then run on the flow cytometer. The percentage of dead cells was measured using flow cytometry and the nucleic acid stain SYTOX® after 24 hours. Over 50% of the bacteria were killed demonstrating the biocidal nature of the high isoprene butyl-based phosphonium ionomer with 0.8 mol % ionic functionality. See FIG. 1.

Example 22

WO 2001/021672, which is incorporated herein by reference, describes the preparation of a brominated butyl terpolymer composed of isobutylene, isoprene and para-methylstyrene. 100 g of brominated terpolymer and 4 g (1.2 molar equivalents based on allylic bromide content of the terpolymer) of triphenylphosphine (TPP) is premixed on a 6"×12" mill at room temperature for 3 minutes. The mixture is then passed through a twin screw extruder at 160° C. The sample is molded at 100° C. for 5 minutes and its resistance to the growth of gram positive (*Staphylococcus aureus*) is tested in triplicate. The samples are placed on Sab Dex agar (SDA) plates where approximately $10^6$ cells are added, plated and incubated at 30° C. After 7 days, no bacterial growth is observed on the sample, demonstrating the inhibition of butyl terpolymer-based phosphonium ionomer with 0.8 mol % ionic functionality to the growth of gram positive bacteria.

Example 23

The resistance of the ionomer formed in Example 22 to gram negative bacteria (*Escherichia coli*) is tested using the same procedure as outlined in Example 22. After 7 days, no bacterial growth is observed on the sample, demonstrating the inhibition of butyl terpolymer-based phosphonium ionomer with 0.8 mol % ionic functionality to the growth of gram negative bacteria.

Example 24

Example 1 was mixed with Carbon Black N660 in a Brabender mixer at 60° C. and a rotor speed of 60 rpm for 15 minutes. The resulting material was molded at 100° C. for 5 minutes and its resistance to the growth of gram positive (*Staphylococcus aureus*, concentration ~$10^5$) was tested in triplicate according to Japanese Industrial Standard JIS Z 2801:00 which is incorporated herein by reference. According to this method, the antibacterial activity is measured by quantifying the survival of bacterial cells which have been held in intimate contact for 24 hours at 35° C. with a surface of the article being tested. The antibacterial effect is measured by comparing the survival of bacteria on the article being tested with that achieved on a control article. In all experiments, the control article consisted of a polyethylene film. There was t least one log reduction of bacteria, displaying the antibacterial nature of carbon-black filled phosphonium ionomer composites to the growth of gram positive bacteria.

Example 25

The resistance of the ionomer formed in Example 24 to gram negative bacteria (*Escherichia coli*) was tested using the same procedure as outlined in Example 24. At least one log reduction of bacteria, displaying the antibacterial nature of carbon-black filled phosphonium ionomer composites to the growth of gram negative bacteria.

Example 26

Example 1 was mixed with Hi Sil 233 in a Brabender mixer at 60° C. and a rotor speed of 60 rpm for 15 minutes. The resulting material was molded at 100° C. for 5 minutes and its resistance to the growth of gram positive (*Staphylococcus aureus*, concentration ~$10^5$) was tested in triplicate according to JIS Z 2801. At least one log reduction of bacteria, displaying the antibacterial nature of silica-filled phosphonium ionomer composites to the growth of gram positive bacteria.

Example 27

The resistance of the ionomer formed in Example 24 to gram negative bacteria (*Escherichia coli*) was tested using the same procedure as outlined in Example 26. At least one log reduction of bacteria, displaying the antibacterial nature of silica-filled phosphonium ionomer composites to the growth of gram negative bacteria.

Example 28

Example 1 was mixed with Cloisite 15A in a Brabender mixer at 60° C. and a rotor speed of 60 rpm for 15 minutes. The resulting material was molded at 100° C. for 5 minutes and its resistance to the growth of gram positive (*Staphylococcus aureus*, concentration ~$10^5$) was tested in triplicate according to JIS Z 2801. At least one log reduction of bacteria, displaying the antibacterial nature of clay-filled phosphonium ionomer nanocomposites to the growth of gram positive bacteria.

Example 29

The resistance of the ionomer formed in Example 28 to gram negative bacteria (*Escherichia coli*) was tested using the same procedure as outlined in Example 28. At least one log reduction of bacteria, displaying the antibacterial nature of silica-filled phosphonium ionomer nanocomposites to the growth of gram negative bacteria.

Example 30

250 g of Exxpro 3745 is combined with 20 g of triphenylphosphine on a room temperature mill for 3 min. The mixture is passed through a miniature twin screw extruder (160° C., 20 rpm) and then refined on a room temperature mill followed by analysis of the resulting material by NMR to confirm the complete conversion of the benzylic bromide groups of the parent polymer to the corresponding ionomeric species. This modified polymer displays resistance to the growth of gram positive bacteria, gram negative bacteria, algae and fungi.

Example 31

A 1 ft$^2$ surface is coated with a butyl ionomer described in Example 1 and is exposed to zebra mussels in an aquarium for 1 week. The number of zebra mussels attached to the surface are counted and compared with a control that is not coated with the butyl ionomer. The butyl ionomer material is successful in preventing the accumulation of zebra mussels if the number of zebra mussels on the ionomer is at most 50% that of the control. It is predicted that the butyl rubber ionomer will be effective in reducing populations or preventing increases in population of mollusca and/or arthropoda, based on previous observations with bacteria, fungi and algae and based on an expected similarly in mechanistic behavior. In particular, it is expected that the ionomer will be effective in preventing attachment of mollusca and arthropoda.

Example 32

100 phr of Example 1 is mixed with 40 phr of Polypropylene in an internal mixer at 180° C. and a rotor speed of 100 rpm. The resulting material is molded and the tensile properties determined. This article displays resistance to the growth of gram positive bacteria, gram negative bacteria, algae and fungi.

Example 33

100 phr of Example 1 is combined with 60 phr Carbon Black N660 in a Banbury mixer at 30° C. and a rotor speed of 77 rpm for 1 minute, followed by the addition of the Pentayln A (4 phr), Sunpar (7 phr), and Vulkacit DM/C (1.3 phr) mixed for an additional 4 minutes. The curatives-sulfur (0.5 phr), stearic acid (1 phr) and zinc oxide (1.5 phr) are then added on a two roll 10"×20" mill and at room temperature. The resulting mixture is cured at 160° C. This cured article displays resistance to the growth of gram positive bacteria, gram negative bacteria, algae and fungi.

What is claimed is:

1. A method of reducing a population of and/or preventing accumulation of organisms on at least a surface of an article, the method comprising painting a butyl ionomer on at least the surface of the article in an amount sufficient to exhibit a reduction of a population of gram negative bacteria by at least 50% when incubated at 30° C. for 24 hours.

2. The method according to claim 1, wherein the ionomer prevents accumulation by preventing an increase in population of the organisms.

3. The method according to claim 1, wherein the ionomer prevents accumulation by impeding attachment of the organisms to the article.

4. The method according to claim 1, wherein the ionomer reduces the population of the organisms by killing individual organisms or inhibiting reproduction of the organisms.

5. The method according to claim 1, wherein the organisms comprise bacteria.

6. The method according to claim 1, wherein the organisms comprise fungi or algae.

7. The method according to claim 1, wherein the ionomer is provided in an amount sufficient to exhibit one or more of the following:
   a. prevention of an increase in the population of gram positive bacteria on the article when incubated in the presence of gram positive bacteria at 30° C. for 7 days;
   b. prevention of an increase in the population of gram negative bacteria on the article when incubated in the presence of gram positive bacteria at 30° C. for 7 days;
   c. prevention of an increase in the population of fungi on the article when incubated in the presence of fungi at 30° C. for 28 days; or,
   d. prevention of an increase in the population of algae on the article when incubated in the presence of algae at 30° C. for 28 days.

8. The method according to claim 1, wherein the ionomer has an ionic content of at least 0.2 mol %.

9. The method according to claim 1, wherein the ionomer comprises a cationic nitrogen based functional group derived from a nitrogen based nucleophile.

10. The method according to claim 1, wherein the ionomer comprises a cationic phosphorus based functional group derived from a phosphorus based nucleophile.

11. The method according to claim 1, wherein the butyl ionomer comprises repeating units derived from an isoolefin monomer and a conjugated diene monomer.

12. The method according to claim 11, wherein the isoolefin monomer comprises isobutylene and the conjugated diene monomer comprises isoprene.

13. The method according to claim 1, wherein the butyl ionomer is provided as part of a composite material that comprises a plastic.

14. The method according to claim 13, wherein the composite material comprises a thermoplastic vulcanizate.

15. The method according to claim 1, wherein preventing the accumulation of the organism comprises preventing the formation of a continuous layer of organisms over greater than 50% of the surface of the article.

* * * * *